US009931790B2

(12) United States Patent
Grbic et al.

(10) Patent No.: US 9,931,790 B2
(45) Date of Patent: Apr. 3, 2018

(54) METHOD AND SYSTEM FOR ADVANCED TRANSCATHETER AORTIC VALVE IMPLANTATION PLANNING

(71) Applicant: Siemens Healthcare GmbH, Erlangen (DE)

(72) Inventors: Sasa Grbic, Plainsboro, NJ (US); Razvan Ionasec, Nuremberg (DE); Tommaso Mansi, Plainsboro, NJ (US); Ingmar Voigt, Erlangen (DE); Dominik Neumann, Erlangen (DE); Julian Krebs, Moers (DE); Chris Schwemmer, Forchheim (DE); Max Schoebinger, Hirschaid (DE); Helene C. Houle, San Jose, CA (US); Dorin Comaniciu, Princeton Junction, NJ (US); Joel Mancina, Singapore (SG)

(73) Assignee: Siemens Healthcare GmbH, Erlangen (DE)

( * ) Notice: Subject to any disclaimer, the term of this patent is extended or adjusted under 35 U.S.C. 154(b) by 340 days.

(21) Appl. No.: 14/688,161

(22) Filed: Apr. 16, 2015

(65) Prior Publication Data
US 2016/0303804 A1 Oct. 20, 2016

(51) Int. Cl.
*B29C 67/00* (2017.01)
*A61F 2/24* (2006.01)
(Continued)

(52) U.S. Cl.
CPC ........ *B29C 67/0088* (2013.01); *A61B 5/1076* (2013.01); *A61F 2/2412* (2013.01);
(Continued)

(58) Field of Classification Search
CPC . B29C 67/0088; G06T 19/00; G05B 19/4099; A61F 2/2496
(Continued)

(56) References Cited

U.S. PATENT DOCUMENTS 6,112,109 A * 8/2000 D'Urso ............... A61F 2/30942
128/898
7,558,611 B2 * 7/2009 Arnold ................. G06T 7/0012
128/922
(Continued)

FOREIGN PATENT DOCUMENTS

WO WO03046833 A2 6/2003

OTHER PUBLICATIONS

Daniel Schmauss et al:"Three-Dimensional Printing of Models for Preoperative Planning and Simulation of Transcatheter Valve Replacement"; The Annals of Thoracic Surgery, Elsevier, US; vol. 93; No. 2; pp. e31-e33, Sep. 9, 2011.
(Continued)

*Primary Examiner* — Chun Cao

(57) ABSTRACT

A method and system for transcatheter aortic valve implantation (TAVI) planning is disclosed. An anatomical surface model of the aortic valve is estimated from medical image data of a patient. Calcified lesions within the aortic valve are segmented in the medical image data. A combined volumetric model of the aortic valve and calcified lesions is generated. A 3D printed model of the heart valve and calcified lesions is created using a 3D printer. Different implant device types and sizes can be placed into the 3D printed model of the aortic valve and calcified lesions to select an implant device type and size for the patient for a TAVI procedure. The method can be similarly applied to other heart valves for any type of heart valve intervention planning.

37 Claims, 7 Drawing Sheets

(51) Int. Cl.
*A61B 5/107* (2006.01)
*G05B 19/4099* (2006.01)
*G09B 23/28* (2006.01)
*B33Y 80/00* (2015.01)
*B33Y 50/00* (2015.01)
*G06T 19/00* (2011.01)
*G06T 7/00* (2017.01)
*G06T 7/73* (2017.01)
*G06T 7/11* (2017.01)
*G06T 7/136* (2017.01)
*B33Y 50/02* (2015.01)

(52) U.S. Cl.
CPC ............ *A61F 2/2496* (2013.01); *B33Y 50/00* (2014.12); *B33Y 80/00* (2014.12); *G05B 19/4099* (2013.01); *G06T 7/0012* (2013.01); *G06T 7/11* (2017.01); *G06T 7/136* (2017.01); *G06T 7/75* (2017.01); *G06T 19/00* (2013.01); *G09B 23/285* (2013.01); *A61B 2576/023* (2013.01); *A61F 2/2415* (2013.01); *A61F 2240/002* (2013.01); *B33Y 50/02* (2014.12); *G05B 2219/35134* (2013.01); *G05B 2219/49007* (2013.01); *G06T 2207/10081* (2013.01); *G06T 2207/20081* (2013.01); *G06T 2207/30048* (2013.01)

(58) Field of Classification Search
USPC .......................................................... 700/98
See application file for complete search history.

(56) References Cited

U.S. PATENT DOCUMENTS

| 7,813,785 | B2* | 10/2010 | Okerlund ............... A61B 6/504 |
| | | | 600/425 |
| 7,916,919 | B2 | 3/2011 | Zheng et al. |
| 8,494,245 | B2 | 7/2013 | Liao et al. |
| 8,934,693 | B2 | 1/2015 | Grbic et al. |
| 2008/0101676 | A1 | 5/2008 | Zheng et al. |
| 2009/0177454 | A1* | 7/2009 | Bronstein ............... G06T 17/20 |
| | | | 703/11 |
| 2011/0052026 | A1 | 3/2011 | Liao et al. |
| 2011/0153286 | A1* | 6/2011 | Zaeuner ............. G06F 19/3437 |
| | | | 703/1 |
| 2013/0129173 | A1 | 5/2013 | Grbic et al. |
| 2013/0155064 | A1 | 6/2013 | Grbic et al. |
| 2013/0231564 | A1 | 9/2013 | Zagorchev et al. |
| 2015/0025666 | A1* | 1/2015 | Olivieri .................. B33Y 50/00 |
| | | | 700/98 |
| 2016/0128786 | A1* | 5/2016 | Weber ..................... G06T 7/251 |
| | | | 382/128 |

OTHER PUBLICATIONS

D. Schmauss et al: "Three-dimensional printing in cardiac surgery and interventional cardiology: a single-centre experience", European Journal of Cardio-Thoracic Surgery; vol. 47, No. 6; pp. 1044-1052, Aug. 26, 2014.

* cited by examiner

300

700　　　710　　　720

800　　　810　　　820

METHOD AND SYSTEM FOR ADVANCED TRANSCATHETER AORTIC VALVE IMPLANTATION PLANNING

BACKGROUND OF THE INVENTION

The present invention relates to transcatheter aortic valve implantation (TAVI) planning, and more particularly, to generating a personalized 3D-printed anatomical model of the aortic valve for planning a TAVI procedure.

Transcatheter aortic valve implantation (TAVI) is becoming the standard choice of care for non-operable and high-risk patients suffering from severe aortic valve stenosis. TAVI is a minimally invasive cardiac intervention in which an aortic valve implant is delivered into a patient through the patient's vessels via a catheter. As there is no direct view or access to the affected anatomy in a TAVI procedure, accurate pre-operative planning is crucial for a successful outcome. Computed tomography (CT) has been established as the gold standard imaging modality for pre-operative planning for TAVI procedures. Standard clinical measurements, such as annular diameters and hinge-annulus plane distance can be estimated based on geometric models derived and used during clinical decision making. One important aspect of the clinical decision making is selecting the right implant device and device size. As dozens of different devices are available on the market and each device comes in different sizes, there are a large number of options for a patient. In addition, due to calcium within the aortic valve, it may not be enough to assess solely the geometric properties of the patient's aortic valve in order to select the right implant device.

BRIEF SUMMARY OF THE INVENTION

The present invention provides a method and system for transcatheter aortic valve implantation (TAVI) planning. Embodiments of the present invention provide an automated framework to extract geometric models of the aortic valve, including calcium, from operative medical image data, that can be printed using a 3D single or multi-material printer to create a physical 3D model of a patient's aortic valve. The final printed 3D model can be created using two different materials representing the two main tissues within valves of stenotic patients of aortic tissue (softer tissue) and calcium (stiffer tissue). Embodiments of the present invention allow for a seamless and fast workflow to go from medical images (e.g., CT images) to 3D printed models within minimal or no user interaction. Based on the printed 3D model of the patient's aortic valve, hands-on preoperative planning for TAVI procedures can be performed, including trying different types of implant devices and different sizes for each type of implant device.

In one embodiment of the present invention, an anatomical surface model of a heart valve is estimated from medical image data of a patient. Calcified lesions within the heart valve are segmented in the medical image data. A combined volumetric model of the heart valve and calcified lesions is generated. A 3D printed model of the heart valve and calcified lesions is created using a 3D printer.

These and other advantages of the invention will be apparent to those of ordinary skill in the art by reference to the following detailed description and the accompanying drawings.

DETAILED DESCRIPTION

The present invention relates to transcatheter aortic valve implantation (TAVI) planning. Embodiments of the present invention are described herein to give a visual understanding of the TAVI planning method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide an automated framework to extract geometric models of the aortic valve, including calcium, from operative medical image data, that can be printed using a 3D single or multi-material printer to create a physical 3D model of a patient's aortic valve. The final printed 3D model can be created using two different materials representing the two main tissues within valves of stenotic patients of aortic tissue (softer tissue) and calcium (stiffer tissue). Embodiments of the present invention allow for a seamless and fast workflow to go from medical images (e.g., CT images) to 3D printed models within minimal or no user interaction. Based on the printed 3D model of the patient's aortic valve, hands-on preoperative planning for TAVI procedures can be performed, including trying different types of implant devices and different sizes for each type of implant device. This allows a user to assess the impact of oversizing or under-sizing a device for a specific patient, as compared to selecting a device size based only on standard clinical measurements. The 3D printed model of the patient's aortic valve can add significant value to the clinical decision making, especially in cases of complex anatomical deformation (e.g., a small annulus but a large dilated aortic valve root) where standard clinical measurements may not be sufficient to select the best implant device and the best size for the implant device. By generating a 3D printed model of the patient's aortic valve in which calcium and normal tissue are printed in separate materials with different material stiffness, the 3D printed model can be effectively utilized to assess the impact of the patient-specific geometry on the deployment of a particular device. In addition, the distance from the device to the coronary ostias can be easily assessed using the printed 3D model.

Figure 1:
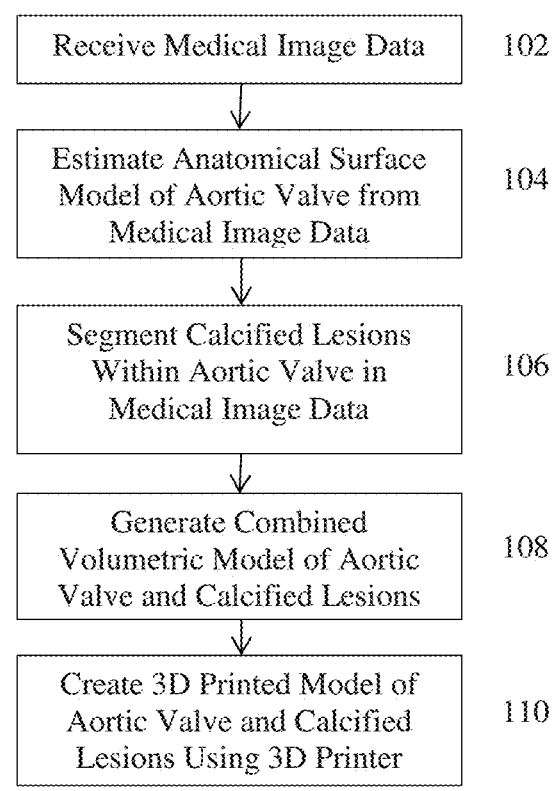
FIG. 1 illustrates a method for transcatheter aortic valve implantation (TAVI) planning according to an embodiment of the present invention.
Figure 2:
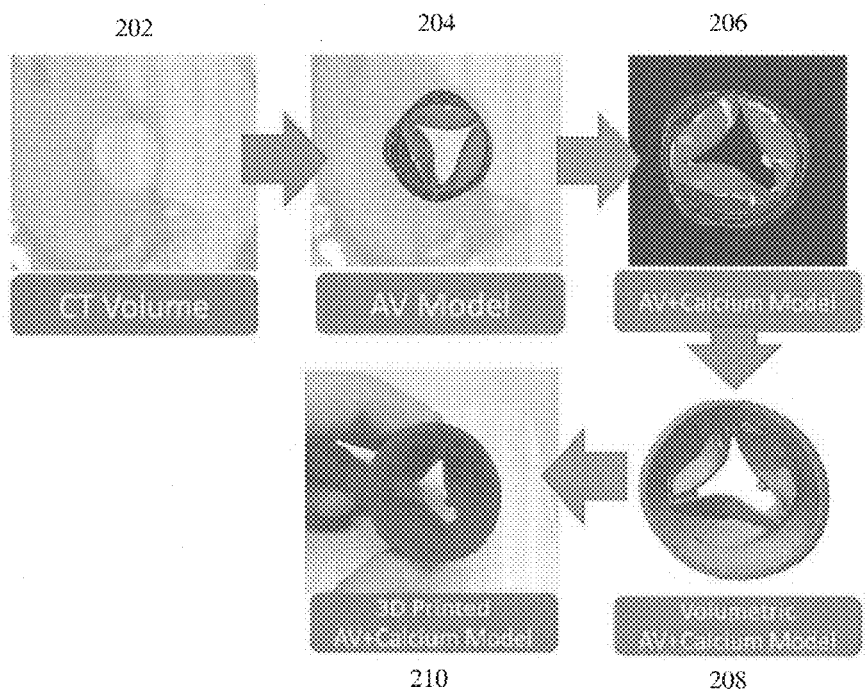
FIG. 2 illustrates exemplary results for the steps of the method of FIG. 1.

FIG. 1 illustrates a method for transcatheter aortic valve implantation (TAVI) planning according to an embodiment of the present invention according to an embodiment of the present invention. The method of FIG. 1 transforms medical image data of a patient into a patient-specific printed 3D model of the patient's aortic valve. The method of FIG. 1 provides anatomical modeling of the patient's aortic valve root, three leaflets, and calcified lesions. FIG. 2 illustrates exemplary results for the steps of the method of FIG. 1. Referring to FIG. 1, at step 102, medical image data of a patient is received. The medical image data can be a pre-operative 3D volume including at least a cardiac region of a patient. According to an advantageous implementation, the medical image data can be a 3D computed tomography (CT) volume, but the present invention is not limited thereto and other imaging modalities, such as magnetic resonance imaging (MRI), ultrasound, DynaCT, etc., can be used as well. The medical image data can be received directly from an image acquisition device, such as a CT scanner, MR scanner, etc., or can be received by loading or receiving over a network previously stored medical image data of the patient. Image 202 of FIG. 2 shows a CT volume of a cardiac region of a patient.

Figure 3:
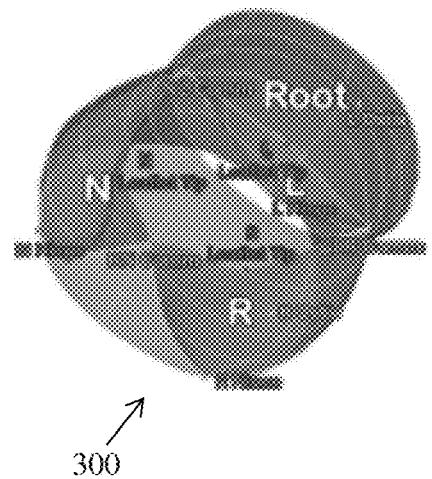
FIG. 3 illustrates a physiological model of the aortic valve, according to an embodiment of the present invention.

At step 104, an anatomical surface model of the aortic valve of the patient is segmented from the medical image data of the patient. In an advantageous embodiment, the surface geometry of patient-specific model of the aortic valve, including the aortic valve root, the three aortic valve leaflets, and the left ventricle outflow tract, is estimated from the medical image data of the patient. Image 204 of FIG. 2 illustrates an exemplary aortic valve surface model extracted from the CT volume 202. In order to estimate the patient-specific surface geometry of the aortic valve, a physiological model of the aortic valve that is capable of capturing complex morphological and pathological variations is fit to the medical image data (e.g., CT volume). FIG. 3 illustrates a physiological model 300 of the aortic valve, according to an embodiment of the present invention. In an exemplary implementation, the aortic valve model 300 can be constructed from 11 landmarks (3 commissures, 3 hinges, 3 leaflet tips, and 2 ostias) and four surface structures (aortic root, N-leaflet, L-leaflet, and R-leaflet). The aortic root surface structure is constrained by the hinge and the commissure plane, and each leaflet surface structure spans between two commissures and one hinge. The left ventricle outflow tract is located at a bottom surface of the aortic root. To efficiently handle the anatomical complexity, the model representation and corresponding parameterization is constructed hierarchically and includes: a global affine model, a non-rigid landmark model m representing the anatomical landmarks, and a full surface model M of the aortic valve including the aortic root and the three leaflets. The patient-specific parameters of the physiological aortic valve model 300 can be estimated from a 3D volume (e.g., CT volume) using robust machine-learning algorithms using hierarchical approaches within a Marginal Space Learning (MSL) framework.

The global position of the aortic valve model in a 3D volume is parameterized with a similarity transformation in the three-dimensional Cartesian space:

$$\Theta = \{(c_x, c_y, c_z), (\vec{\alpha}_x, \vec{\alpha}_y, \vec{\alpha}_z), (s_x, s_y, s_z)\} \quad (1)$$

where $(c_x, c_y, c_z), (\vec{\alpha}_x, \vec{\alpha}_y, \vec{\alpha}_z)$, and $(s_x, s_y, s_z)$ are the position, orientation, and scale parameters, respectively. The position is given by the aortic valve's gravity center, while scale parameters are chosen such that the entire anatomy of the aortic valve is included in a bounding box corresponding to the affine parameterization. The orientation of the long axes is defined by the normal vectors to the aortic-commissural plane, while the short axes are oriented to point from the gravity center to the LR-commissure. The next complexity level of the aortic valve model can be modeled by 11 anatomical landmarks: R-, N-, and L-hinges, and LR-, RN-, NL-commissures, R-, N-, and L-leaflet tips, and R- and L-ostia. The highest abstraction layer of the aortic valve model models the 3D surfaces of the aortic root, and the N-, L-, and R-leaflets. The aortic root surface is represented by a tubular grid, which is aligned with the aortic circumferential direction μ and ascending directions ν. Each of the leaflet surfaces is represented as a paraboloid fixed to the root on an attachment crown delineated by the hinges and commissures with the remaining free edge constrained by the corresponding leaflet tip point.

Figure 4:
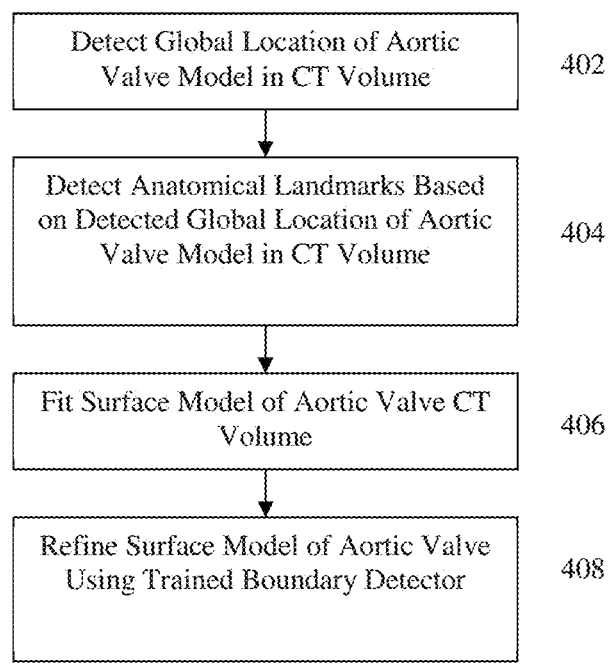
FIG. 4 illustrates a method for segmenting an anatomical surface model of the aortic valve surface model in a CT volume according to an embodiment of the present invention.

In order to maximize efficiency and comply with the hierarchical model definition, the patient specific aortic valve model can be estimated in the medical image data of the patient using an estimation algorithm that is based on robust learning methods and includes a global localization stage, an anatomical landmark estimation stage, and a surface model fitting stage. FIG. 4 illustrates a method for estimating a patient-specific anatomical surface model of the aortic valve in a CT volume according to an embodiment of the present invention. The method of FIG. 4 can be used to implement step 104 of FIG. 1. Although the method of FIG. 4 describes estimating the patient-specific anatomical surface model in a CT volume, it is to be understood that the method of FIG. 4 can be similarly applied to other types of volumetric medical image data as well.

Referring to FIG. 3, at step 402, the global location of the aortic valve model is detected in the CT volume. The global location is represented by the 3D affine parameters $(c_x, c_y, c_z, \alpha_x, \alpha_y, \alpha_z, s_x, s_y, s_z)$. These parameters define a bounding box corresponding to the global location of the aortic valve model in the CT volume, and are defined by combining anatomy detectors trained using the Marginal Space Learning (MSL) framework. MSL provides an efficient technique for learning high dimensional models and fast online searching by operating in subspaces of increasing dimensionality:

$$\Sigma_1 = (c_x, c_y, c_z)$$
$$\Sigma_2 = (c_x, c_y, c_z, \vec{\alpha}_x, \vec{\alpha}_y, \vec{\alpha}_z)$$
$$\Sigma_3 = (c_x, c_y, c_z, \vec{\alpha}_x, \vec{\alpha}_y, \vec{\alpha}_z, s_x, s_y, s_z).$$

Accordingly, the idea of MSL is not to learn a classifier directly in the full similarity transformation space, but to incrementally learn classifiers in the series of marginal spaces. As the dimensionality increases, the valid space region becomes more restricted by previous marginal space classifiers. The 3D object detection (global location estimation) is split into three steps: object position estimation, position-orientation estimation, and position-orientation-scale estimation. A separate classifier is trained based on annotated training data for each of these steps. Each classifier can be trained using a probabilistic boosting tree (PBT) in combination with Haar and/or steerable features based on a set of annotated training data. This results in the estimated affine transformation (position, orientation, and scale) defining a bounding box representing the global location of the aortic valve model in the CT volume. MSL is described in greater detail in U.S. Pat. No. 7,916,919, issued Mar. 29, 2011, and entitled "System and Method for Segmenting Chambers of a Heart in a Three Dimensional Image", which is incorporated herein by reference. In an exemplary implementation, the estimation of the global location of the aortic valve model can be performed on a 3 mm resolution.

At step 404, anatomic landmarks are detected in the 3D CT volume based on the detected global location of the aortic valve model. In particular, constrained by the global location $\Theta$, the 11 aortic valve landmarks $m_1 \ldots m_{11}$ are detected in the CT volume using respective trained landmark detectors. An independent landmark detector is trained for each of the 11 aortic valve landmarks (3 commissures, 3 hinges, 3 leaflet tips, and 2 ostias). Each landmark detector can be trained as a PBT classifier using Haar features based on annotated training data. In an advantageous embodiment, positive and negative training samples for training each landmark detector are extracted only from detected global location regions of training images. The trained landmark detectors search for the respective landmarks in a smaller subspace of the CT volume constrained by the detected global location $\Theta$:

$$p(m_i|I(t)) = p(m_i|\Theta(t), I(t)) \; i=1 \ldots 11. \quad (2)$$

As the search space is constrained to the bounding box corresponding to the detected global location, the landmark detection may be performed on a finer resolution than the global localization. For example, the landmark detection may be performed on a 1 mm isotropic resolution. In this case, the landmark detectors are also trained at the finer resolution.

At step 406, a surface model of the aortic valve is fit to the CT volume. In particular, a surface model including the aortic root surface, the 3 leaflet surfaces, and the left ventricle outflow tract, is fit to the CT volume based on the detected anatomical landmarks. In a possible embodiment, the surface model of the aortic valve may be estimated using a non-rigid MSL framework, in which a search space is defined by a number of modes of a statistical shape model of the aortic valve surface model learned from the ground truth meshes in the set of training data. The statistical shape model can be generated from the training data using principle component analysis (PCA) in order to represent variations in the ground truth aortic valve meshes in the training data. In a possible implementation, the search space for the aortic valve surface model can be defined by the first three modes $(c_1, c_2, c_3)$ of the statistical shape model computed from the training data. Each hypothesis in $c_1, c_2, c_3$ (i.e., each sample point in the statistical shape space) corresponds to a non-rigid shape. In order to learn which coefficients for the statistical shape model best correspond to the shape of the aortic valve in the CT volume, each sample from $c_1, c_2, c_3$ is used to generate a non-rigid shape of the aortic valve, which is projected to the image space using the detected global localization $\Theta$. This results in a set of hypotheses for the aortic valve surface model. A trained classifier is used select the best hypothesis from the set of surface model hypotheses as the aortic valve surface model. This classifier can be a boosting classifier trained based on ground truth aortic root surface models in the training data and steerable features extracted around the non-rigid shape points of the surface model hypotheses. Accordingly, for each surface model hypothesis projected to the detected global location in the CT volume, steerable features are extracted in a neighborhood surrounding each model point and a probability score for the hypothesis is determined by the trained classifier based on the extracted steerable features. The surface model hypothesis having the highest probability score is selected as the aortic valve surface model. In another possible embodiment, the aortic valve surface model can be fit the CT volume by calculating a transformation, such as a thin plate spline (TPS) transformation, based on the detected anatomical landmark points that maps each point in the physiological aortic valve model to a corresponding location in the CT volume.

At step 408, the shape of the aortic valve surface model is locally refined using a trained boundary detector. The trained boundary detector can be trained based on the training data using a PBT classifier and steerable features. The boundary of the aortic valve surface model is refined by applying the trained classifier locally in a neighborhood of each point on the aortic valve surface model to search in a normal direction for a point having a highest probability score.

Figure 5:
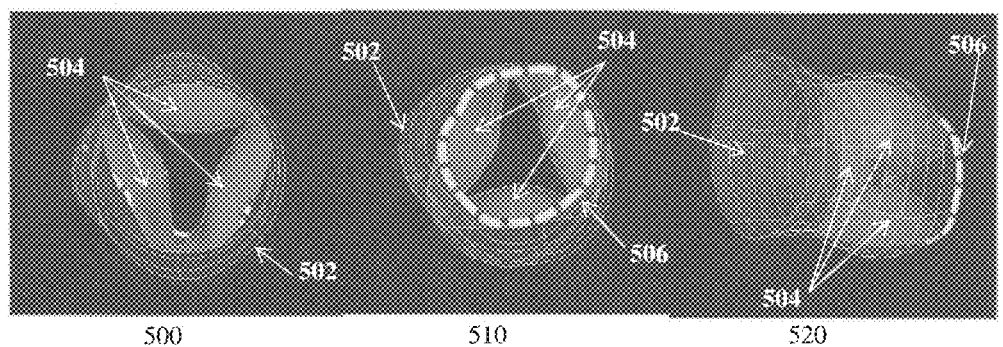
FIG. 5 illustrates an exemplary anatomical surface model of the aortic valve estimated from a CT volume.

FIG. 5 illustrates an exemplary anatomical surface model of the aortic valve estimated from a CT volume. As shown in FIG. 5, images 500, 510, and 520 show a top view, bottom view, and side view, respectively, of a patient-specific anatomical surface model of the aortic valve estimated from a CT volume. The anatomical surface model includes the patient-specific surface geometry of the aortic root 502, leaflets 504, and left ventricle outflow tract 506.

Returning to FIG. 1, at step 106, calcified lesions within the aortic valve are estimated in the medical image data of the patient. A region-of-interest (ROI) of the 3D medical image volume is defined based on the estimated patient-specific surface model of the aortic valve. In particular, the volumetric region defined by the boundaries of the estimate aortic valve surface model can be cropped in order to define a ROI in the 3D medical image volume for segmenting calcified lesions. The calcified lesions are segmented in the defined ROI of the 3D medical image volume. The segmented calcified lesions can be mapped to the patient-specific surface model of the aortic valve. Image 206 of FIG. 2 shows an example of an aortic valve and calcium model resulting from segmenting the calcified lesions. In an advantageous embodiment, intensity thresholding is used to segment the calcified lesions in the aortic valve ROI. The intensity (Hounsfield units) of each voxel in the abortive valve ROI is compared to a calcium threshold, and if the intensity of a voxel is determined to be greater than the calcium threshold, that voxel is determined to be a calcium lesion voxel. For non-contrasted CT volumes (i.e., CT volumes acquired when no contrast agent has been injected into the patient), a predetermined calcium threshold value can be used for the intensity thresholding, as the calcified lesions will appear significantly brighter than the aortic valve tissue. For contrast CT volumes (i.e., CT volumes acquired when a contrast agent has been injected into the patient), a predetermined calcium threshold value may not be as accurate.

In an advantageous embodiment, the calcium threshold can be automatically determined for each medical image volume using a machine-learning based method. This technique can determine a calcium threshold for both contrast and non-contrast CT volumes, as well as for other types of imaging modalities. For each of a plurality of training image data sets (e.g., CT volumes), a respective calcium threshold is manually set and a histogram representing the intensity profile is identified. In a possible embodiment, a regression function is trained in an offline training stage based on the training data to calculate a calcium threshold based on histogram features within an aortic valve ROI. For example, the regression function can be trained using Random Forests to learn a relationship between the histogram features within the training images and the calcium thresholds for the training images. For the current medical image data of the patient, a histogram representing the intensity profile in the aortic valve ROI is determined and the regression function calculates the calcium threshold based on histogram features within the aortic valve ROI. In another possible embodiment, a k-nearest neighbor algorithm can be used to determine the calcium threshold. In this case, the histogram representing the intensity profile within the aortic valve ROI is determined for the current image and a k-nearest neighbor algorithm is used to compare the histogram within the aortic valve ROI for the current image with the histograms of the training images in a database in order to find the k (e.g., 3) nearest neighbors to the current image among the training images. The calcium threshold for the current image can then be determined based on the k nearest neighbor training images. For example, the mean of the calcium thresholds of the k nearest neighbor training images can be used as the calcium threshold for the current image.

Figure 6:
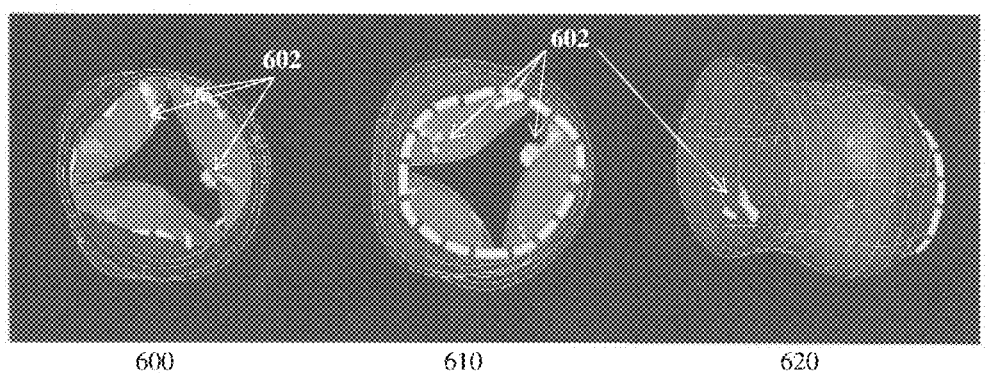
FIG. 6 illustrates exemplary results of segmenting calcified lesions in the aortic valve.

FIG. 6 illustrates exemplary results of segmenting calcified lesions in the aortic valve. As shown in FIG. 6, images 600, 610, and 620 show a top view, bottom view, and side view, respectively, of a patient-specific anatomical surface model of the aortic valve with segmented calcified lesions 602.

Returning to FIG. 1, at step 108, a combined volumetric model of the aortic valve and calcified lesions is generated. The estimated patient-specific surface model of the aortic valve provides 3D boundaries of the aortic valve, but is a flat model with no thickness. The volumetric combined model of the aortic valve and calcified lesions is generated by extruding the surface model of the aortic valve along its normals and including the segmented calcified lesions in the final volumetric model. In particular, at each point on the surface model of the aortic valve, the model is extruded to a particular thickness in a direction normal to the surface at that point. The model can be extruded to a predetermined thickness for the aortic valve root and the aortic valve leaflets. In an exemplary implementation, standard values from literature can be used for the thickness of the aortic valve root and the aortic valve leaflets. The aortic valve root and aortic valve leaflets in the combined volumetric model may be set to have different thicknesses. In another possible implementation, the thickness of one or more portions of the combine volumetric model may be determined based on printer settings of the 3D printer used to print the 3D model of the aortic valve. For example, the thickness of the aortic valve root and/or the aortic valve leaflets may be set to predetermined value (e.g., 8 mm) corresponding to a minimum thickness at which the 3D printer is able to print. In one embodiment, a respective thickness is determined for the aortic root and the valve leaflets using standard thickness values. If the thickness determined for the aortic root or the valve leaflets is smaller than a minimum thickness level of the 3D printer, the thickness is increased to the minimum thickness level of the 3D printer. Since the calcified lesions are segmented in the 3D volume, a thickness is associated with each segmented calcified lesion. If the thickness (in any direction) of a particular calcified lesion is smaller than the minimum thickness level of the 3D printer, that calcified lesion may be expanded to meet the minimum thickness level.

Figure 7:
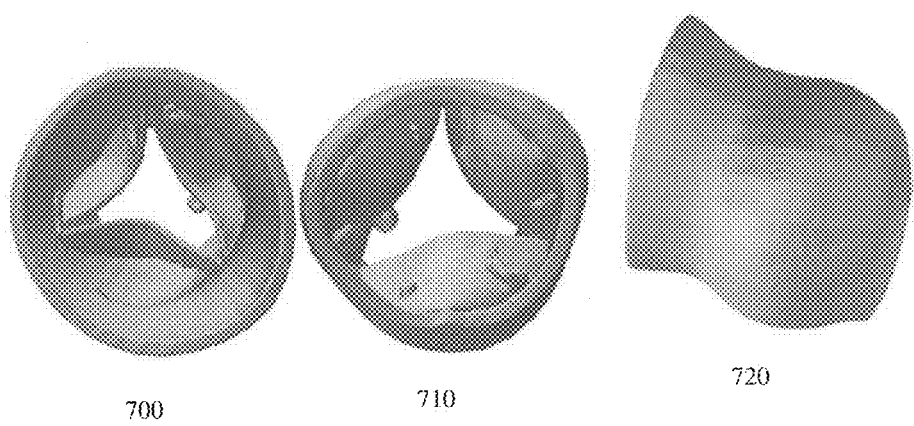
FIG. 7 illustrates an exemplary combined volumetric model of the aortic valve and calcified lesions.

FIG. 7 illustrates an exemplary combined volumetric model of the aortic valve and calcified lesions. As shown in FIG. 7, images 700, 710, and 720 show a top view, bottom view, and side view, respectively, of the combined volumetric model of the aortic valve and calcified lesions.

Returning to FIG. 1, at step 110, a 3D printed model of the aortic valve and calcified lesions is created using a 3D printer. The 3D printed model is a physical patient-specific 3D model of the aortic valve and calcified lesions of the patient that is printed using a 3D printer. Once the combined volumetric model of the aortic valve and calcified lesions is generated with a thickness that satisfies the minimum thickness level of the 3D printer, the combined volumetric model of the aortic valve and calcified lesions can be printed by the 3D printer, resulting in the physical 3D printed model of the aortic valve and calcified lesions. Image 210 of FIG. 1 shows an exemplary 3D printed model of the aortic valve and calcified lesions. The 3D printer can be a single material 3D printer or a multi-material 3D printer. In the case in which a single material 3D printer is used, the 3D printed model can be printed using a flexible material that is similarly flexible to aortic valve tissue. In an advantageous embodiment, a multi-material 3D printer is used to create the 3D printed model and different materials are used for the aortic valve tissue and the calcified lesions. In particular, a first material that is more flexible is used for the aortic valve tissue and a second material that is stiffer is used for the calcified lesions in order to represent the real tissue properties of the different types of tissue. The first material can be a material having a stiffness property (e.g., Young's modulus) equal to or similar to a standard value for a stiffness property of aortic valve tissue, and the second material can be a material having a stiffness property equal to or similar to a standard value for a stiffness property of calcifications. If patient-specific measurements of the stiffness of the aortic valve are available, the first material can be selected as a material having a stiffness property similar to the patient-specific stiffness measurements of the patient's aortic valve.

Figure 8:
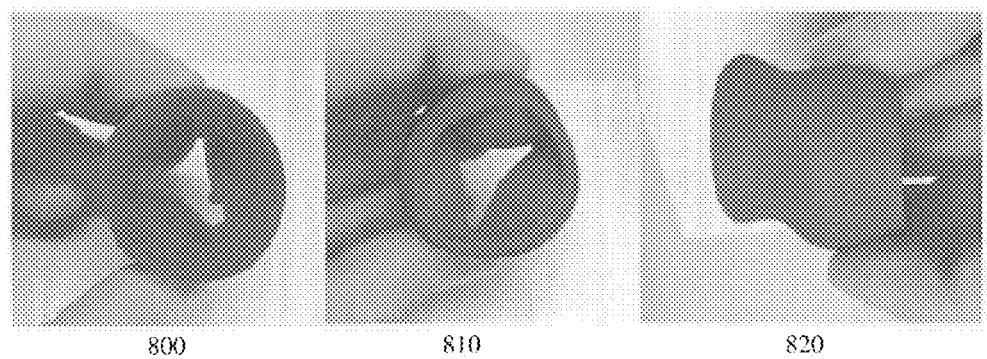
FIG. 8 illustrates an exemplary 3D printed model of the aortic valve and calcified lesions.

FIG. 8 illustrates an exemplary 3D printed model of the aortic valve and calcified lesions. As shown in FIG. 8, images 800, 810, and 820 show a top view, bottom view, and side view, respectively, of the patient-specific 3D printed model of the aortic valve and calcified lesions.

As described above, in the method of FIG. 1, the 3D printed model is generated based on an anatomical surface model of the aortic valve estimated from a 3D medical image volume and calcified lesions segmented in the 3D medical image volume. In various embodiments, the 3D medical image volume can be acquired when the aortic valve is open in order to generate a 3D printed model of an open aortic valve or the 3D medical image volume can be acquired when the aortic valve is closed in order to generate a 3D printed model of a closed aortic valve. It is also possible that multiple 3D printed models are generated by repeating the method of FIG. 1 for various 3D volumes acquired at different times during the cardiac cycle. For example, the medical image data can include a 4D (3D+ time) image sequence (e.g., 4D CT image sequence) acquired over a cardiac cycle, where each frame of the sequence is a 3D volume. The method of FIG. 1 can be repeated for various frames of the 4D image sequence to generate 3D printed models of the aortic valve and calcified lesions in opened and closed position. For example, a first frame acquired during systole can be used to generate a 3D printed model of the aortic valve in an open position and a second frame acquired during diastole can be used to generate a 3D printed model of the aortic valve in a closed position.

The final 3D printed model can be used for a hands-on approach toward TAVI planning. Different implant devices, device types, and device sizes can be placed within the 3D printed model to assess the impact of implant over- and under-sizing. In addition, as described above, the calcified lesions can be printed using a stiffer material than the aortic valve tissue in order to resemble the real tissue properties of the calcified lesions, and thus the effect of the calcified lesions on the final deployment of an implant device can be studied. For example, the calcified lesions may cause under deployment of the valve, which can cause paravalvular leaks and other problems. The workflow described herein can be particularly beneficial for patients with abnormal valve shapes (e.g., small annulus but large dilated aortic valve root) in order to assess the impact of a specific device on the patient prior to the TAVI procedure. In addition to planning TAVI procedures, the 3D printed model of the aortic valve and calcified lesions can also be used for training. For example, the 3D printed model can be used to train physicians in the placement of implants, especially for patients with abnormal valve shapes. The 3D printed model can also be used for device testing of new implant devices. For example, a new implant device can be placed within the 3D printed model in order test various properties of the new implant device, such as durability, functionality, etc. Furthermore, the 3D printed model of the aortic valve and calcified lesions can be used to construct and test personalized implant devices fit to the patient-specific geometry of the 3D printed model.

Figure 9:
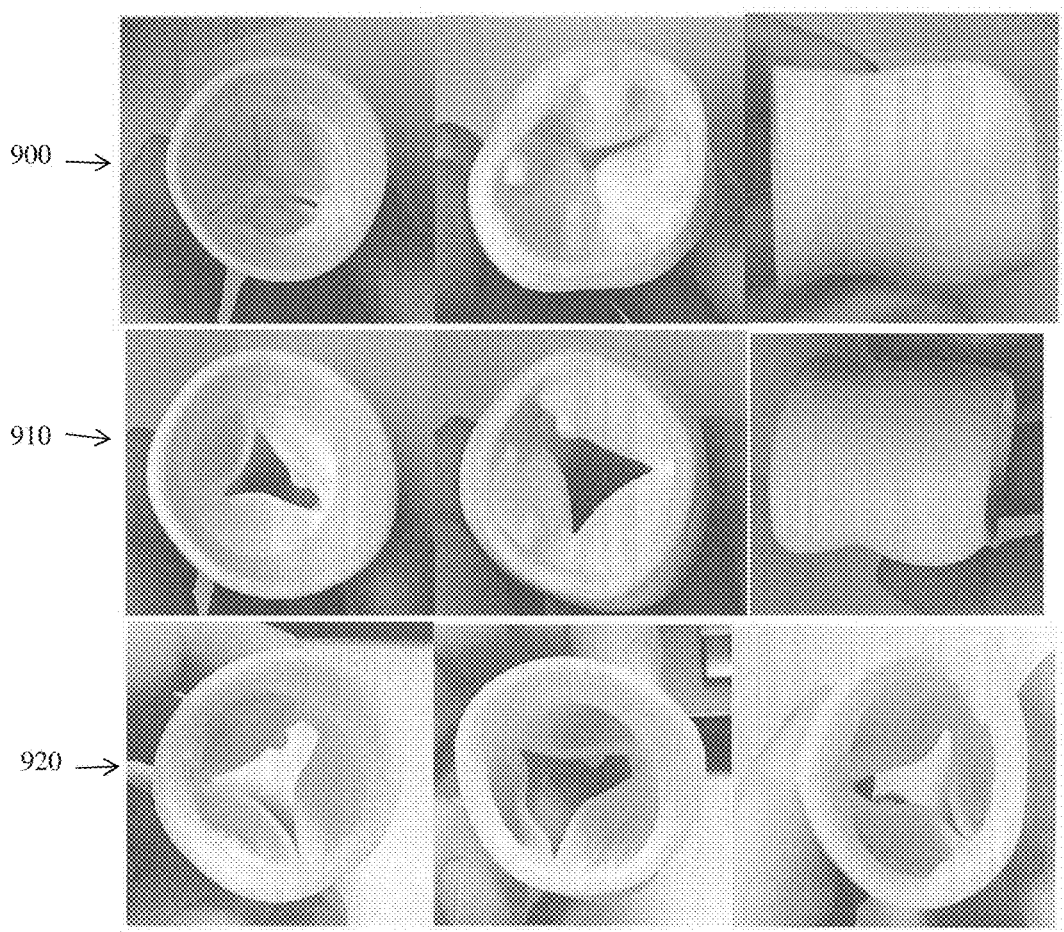
FIG. 9 illustrates additional examples of 3D printed models of aortic valves generated using the method of FIG. 1.

FIG. 9 illustrates additional examples of 3D printed models of aortic valves generated using the method of FIG. 1. As shown in FIG. 9 row 900 shows various views of a patient-specific 3D printed model of the aortic valve and calcified lesions for a first patient, row 910 shows various views of a patient-specific 3D printed model of the aortic valve and calcified lesions for a second patient, and row 920 shows various views of a patient-specific 3D printed model of the aortic valve and calcified lesions for a third patient.

As described above, the method of FIG. 1 creates a 3D printed model of the aortic valve and calcified lesions for patient-specific planning of a TAVI procedure. However, the present invention is not limited to the aortic valve and TAVI planning and the method of FIG. 1 can be similarly applied to any other heart valve (e.g., pulmonary valve, mitral valve, and tricuspid valve) to generate a 3D printed model of the heart valve for patient-specific planning of a heart valve intervention.

Figure 10:
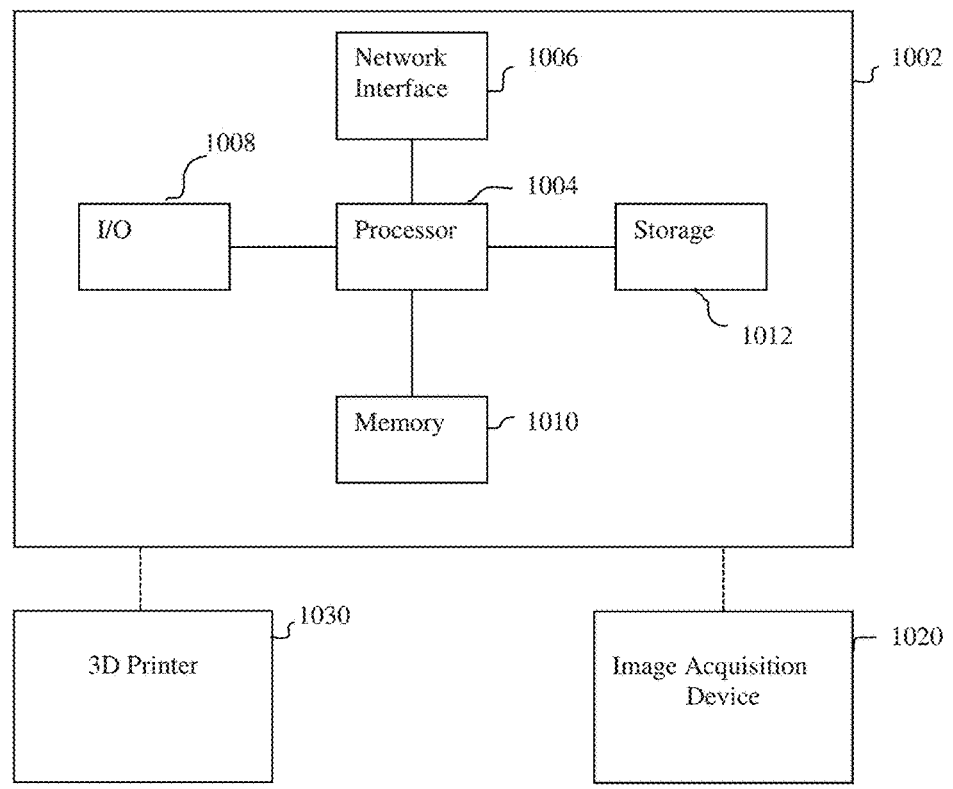
FIG. 10 is a high-level block diagram of an apparatus capable of implementing the present invention.

FIG. 10 is a high-level block diagram of an apparatus capable of implementing the present invention. The above-described methods for planning a heart valve intervention, such as TAVI, may be implemented on a computer 1002 using well-known computer processors, memory units, storage devices, computer software, and other components, in conjunction with a 3D printer 1030. Computer 1002 contains a processor 1004, which controls the overall operation of the computer 1002 by executing computer program instructions which define such operation. The computer program instructions may be stored in a storage device 1012 (e.g., magnetic disk) and loaded into memory 1010 when execution of the computer program instructions is desired. Thus, the steps of the methods of FIGS. 1 and 4 may be defined by the computer program instructions stored in the memory 1010 and/or storage 1012 and controlled by the processor 1004 executing the computer program instructions. An image acquisition device 1020, such as a CT scanner, can be connected to the computer 1002 to input image data to the computer 1002. It is possible to implement the image acquisition device 1020 and the computer 1002 as one device. It is also possible that the image acquisition device 1020 and the computer 1002 communicate wirelessly through a network. In a possible embodiment, the computer 1002 may be located remotely with respect to the image acquisition device 1020 and may perform the method steps as part of a server or cloud based service.

A 3D printer 1030 can be connected to the computer 1002 in order to print a 3D model of an aortic valve or other heart valve. The 3D printer 1030 can be a single material 3D printer or a multi-material 3D printer. The 3D printer 1030 can utilize any type of 3D printing technology including, but not limited to stereolithography, fused deposition modeling, selective laser sintering, selective laser melting, electronic beam melting, or laminated object manufacturing. The 3D printer 1030 may be connected to the computer 1002 via a wired connection or the 3D printer 1030 and the computer 1002 may communicate wirelessly through a network. In one embodiment, the 3D printer 1030 can be located in proximity to the computer 1002 and the image acquisition device 1020, such that all of the method steps of the method of FIG. 1, from image acquisition to creating the 3D printed model, can be performed locally. In another embodiment, the 3D printer 1030 and the computer 1002 can be located remotely with respect to the image acquisition device 1020 and the method steps of FIG. 1 may be performed as part of a server or cloud based service, with the physical 3D printed model sent to a client or user once it is created. In yet another embodiment, the 3D printer 1030 may be located remotely with respect to the computer 1002 and the image acquisition device 1020, such that the method steps of estimating the anatomical surface model of the aortic valve, segmenting the calcified lesions, and generating the combined volumetric model of the aortic valve and the calcified lesions are performed locally by the computer 1002 and the printing of the 3D printed model is performed by 3D printer 1030 as part of a server or cloud based service.

The computer 1002 also includes one or more network interfaces 1006 for communicating with other devices via a network. The computer 1002 also includes other input/output devices 1008 that enable user interaction with the computer 1002 (e.g., display, keyboard, mouse, speakers, buttons, etc.). One skilled in the art will recognize that an implementation of an actual computer could contain other components as well, and that FIG. 10 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:
1. A method for heart valve intervention planning, comprising:
    estimating an anatomical surface model of a heart valve from medical image data of a patient;

segmenting calcified lesions within the heart valve in the medical image data;

generating a combined volumetric model of the heart valve and calcified lesions, wherein generating the combined volumetric model of the heart valve and calcified lesions comprises:

mapping the segmented calcified lesions to the anatomical surface model of the heart valve, and extruding the anatomical surface model of the heart valve to a predetermined thickness; and creating a 3D printed model of the heart valve and calcified lesions using a 3D printer, wherein the heart valve is an aortic valve and extruding the anatomical surface model of the heart valve to a predetermined thickness comprises:

extruding an aortic root surface of the anatomical surface model of the heart valve to a standard thickness associated with the aortic root if the standard thickness associated with the aortic root is greater than or equal to a minimum thickness level associated with the 3D printer;

extruding the aortic root surface of the anatomical surface model of the heart valve to the minimum thickness level associated with the 3D printer if the standard thickness associated with the aortic root is less than the minimum thickness level associated with the 3D printer;

extruding aortic valve leaflet surfaces of the anatomical surface model of the heart valve to a standard thickness associated with the aortic valve leaflets if the standard thickness associated with the aortic valve leaflets is greater than or equal to the minimum thickness level associated with the 3D printer; and extruding the aortic valve leaflet surfaces of the anatomical surface model of the heart valve to the minimum thickness level associated with the 3D printer if the standard thickness associated with the aortic valve leaflets is less than the minimum thickness level associated with the 3D printer.

2. The method of claim 1, wherein creating a 3D printed model of the heart valve and calcified lesions using a 3D printer comprises:

creating the 3D printed model of the heart valve and calcified lesions using a first material for heart valve tissue and a second material for the calcified lesions.

3. The method of claim 2, wherein the second material has a stiffness that is greater than the first material.

4. The method of claim 3, wherein the first material has a stiffness property equal to a standard value of a stiffness property of the heart valve tissue and the second material has a stiffness property equal to a standard value of a stiffness property of calcified lesions.

5. The method of claim 1, wherein estimating an anatomical surface model of a heart valve from medical image data of a patient comprises:

detecting a global location of a physiological model of the heart valve in the medical image data;

detecting anatomical landmarks of the heart valve in the medical image data based on the detected global location; and fitting a surface model of the heart valve to the medical image data based on the detected anatomical landmarks.

6. The method of claim 5, wherein estimating an anatomical surface model of a heart valve from medical image data of a patient further comprises:

refining the surface model of the heart valve using a trained boundary detector.

7. The method of claim 5, wherein detecting anatomical landmarks of the heart valve in the medical image data based on the detected global location comprises:

detecting commissure landmarks, hinge landmarks, leaflet tip landmarks, and ostia landmarks of the aortic valve in a region of the medical image data constrained based on the detected global location.

8. The method of claim 7, wherein fitting a surface model of the heart valve to the medical image data based on the detected anatomical landmarks comprises:

fitting surface models of an aortic root and aortic valve leaflets to the medical image data based on the detected commissure landmarks, hinge landmarks, leaflet tip landmarks, and ostia landmarks.

9. The method of claim 1, wherein segmenting calcified lesions within the heart valve in the medical image data comprises:

defining a heart valve region-of-interest in the medical image data based on the estimated anatomical surface model of the heart valve; and segmenting the calcified lesions within the heart valve region-of-interest in the medical image data.

10. The method of claim 9, wherein segmenting the calcified lesions within the heart valve region-of-interest in the medical image data comprises:

detecting voxels in the heart valve region-of-interest having intensity values greater than a calcium threshold.

11. The method of claim 10, wherein segmenting the calcified lesions within the heart valve region-of-interest in the medical image data further comprises:

determining the calcium threshold based on an intensity histogram in the heart valve region-of-interest of the medical image data.

12. The method of claim 11, wherein determining the calcium threshold based on an intensity histogram in the heart valve region-of-interest of the medical image data comprises:

determining the intensity histogram in the heart valve region-of-interest of the medical image data; and calculating the calcium threshold based on the intensity histogram in the heart valve region-of-interest of the medical image data using a trained regression function.

13. The method of claim 11, wherein determining the calcium threshold based on an intensity histogram in the heart valve region-of-interest of the medical image data comprises:

determining the intensity histogram in the heart valve region-of-interest of the medical image data;

identifying a number of nearest neighbor training images in a database of training images based on the intensity histogram in the heart valve region-of-interest of the medical image data; and calculating a mean of calcium thresholds associated with the number of nearest neighbor training images.

14. The method of claim 1, wherein extruding the anatomical surface model of the heart valve to a predetermined thickness further comprises:

at each of a plurality of points on the anatomical surface model of the heart valve, extruding the anatomical surface model of the heart valve in a direction normal to the anatomical surface model of the heart valve.

15. The method of claim 1, wherein extruding the anatomical surface model of the heart valve to a predetermined thickness further comprises:

expanding at least one of the segmented calcified lesions to the minimum thickness level associated with the 3D printer.

16. The method of claim 1, wherein creating a 3D printed model of the heart valve and calcified lesions using a 3D printer comprises:
   printing a physical 3D model of the combined volumetric model of the heart valve and calcified lesions using the 3D printer.

17. The method of claim 1, further comprising:
   placing a plurality of different implant device types and implant device sizes into the 3D printed model of the heart valve and calcified lesions to select an implant device type and size for the patient for a heart valve intervention procedure.

18. An apparatus for heart valve intervention planning, comprising:
   a processor;
   a memory storing computer program instructions, which when executed by the processor cause the processor to perform operations comprising:
      estimating an anatomical surface model of a heart valve from medical image data of a patient,
      segmenting calcified lesions within the heart valve in the medical image data, and
   generating a combined volumetric model of the heart valve and calcified lesions, wherein generating the combined volumetric model of the heart valve and calcified lesions comprises:
      mapping the segmented calcified lesions to the anatomical surface model of the heart valve, and
      extruding the anatomical surface model of the heart valve to a predetermined thickness; and
   a 3D printer for creating a 3D printed model of the heart valve and calcified lesions,
   wherein the heart valve is an aortic valve and extruding the anatomical surface model of the heart valve to a predetermined thickness comprises:
      extruding an aortic root surface of the anatomical surface model of the heart valve to a standard thickness associated with the aortic root if the standard thickness associated with the aortic root is greater than or equal to a minimum thickness level associated with the 3D printer,
      extruding the aortic root surface of the anatomical surface model of the heart valve to the minimum thickness level associated with the 3D printer if the standard thickness associated with the aortic root is less than the minimum thickness level associated with the 3D printer,
      extruding aortic valve leaflet surfaces of the anatomical surface model of the heart valve to a standard thickness associated with the aortic valve leaflets if the standard thickness associated with the aortic valve leaflets is greater than or equal to the minimum thickness level associated with the 3D printer, and
      extruding the aortic valve leaflet surfaces of the anatomical surface model of the heart valve to the minimum thickness level associated with the 3D printer if the standard thickness associated with the aortic valve leaflets is less than the minimum thickness level associated with the 3D printer.

19. The apparatus of claim 18, wherein the 3D printer comprises:
   a multi-material 3D printer for creating the 3D printed model of the heart valve and calcified lesions using a first material for heart valve tissue and a second material for the calcified lesions.

20. The apparatus of claim 19, wherein the second material has a stiffness that is greater than the first material.

21. The apparatus of claim 20, wherein the first material has a stiffness property equal to a standard value of a stiffness property of the heart valve tissue and the second material has a stiffness property equal to a standard value of a stiffness property of calcified lesions.

22. The apparatus of claim 18, wherein estimating an anatomical surface model of a heart valve from medical image data of a patient comprises:
   detecting a global location of a physiological model of the heart valve in the medical image data;
   detecting anatomical landmarks of the heart valve in the medical image data based on the detected global location; and
   fitting a surface model of the heart valve to the medical image data based on the detected anatomical landmarks.

23. The apparatus of claim 18, wherein segmenting calcified lesions within the heart valve in the medical image data comprises:
   defining a heart valve region-of-interest in the medical image data based on the estimated anatomical surface model of the heart valve; and
   segmenting the calcified lesions within the heart valve region-of-interest in the medical image data.

24. The apparatus of claim 23, wherein segmenting the calcified lesions within the heart valve region-of-interest in the medical image data comprises:
   detecting voxels in the heart valve region-of-interest having intensity values greater than a calcium threshold.

25. The apparatus of claim 24, wherein segmenting the calcified lesions within the heart valve region-of-interest in the medical image data further comprises:
   determining the calcium threshold based on an intensity histogram in the heart valve region-of-interest of the medical image data.

26. The apparatus of claim 18, wherein extruding the anatomical surface model of the heart valve to a predetermined thickness further comprises:
   at each of a plurality of points on the anatomical surface model of the heart valve, extruding the anatomical surface model of the heart valve in a direction normal to the anatomical surface model of the heart valve.

27. The apparatus of claim 18, wherein the 3D printer creates the 3D printed model of the heart valve and calcified lesion by printing a physical 3D model of the combined volumetric model of the heart valve and calcified lesions using the 3D printer.

28. A non-transitory computer readable medium storing computer program instructions for heart valve intervention planning, the computer program instructions when executed by a processor cause the processor to perform operations comprising:
   estimating an anatomical surface model of a heart valve from medical image data of a patient;
   segmenting calcified lesions within the heart valve in the medical image data;
   generating a combined volumetric model of the heart valve and calcified lesions, wherein generating the combined volumetric model of the heart valve and calcified lesions comprises:
      mapping the segmented calcified lesions to the anatomical surface model of the heart valve, and extruding the anatomical surface model of the heart valve to a predetermined thickness; and controlling a 3D printer to create a 3D printed model of the heart valve and calcified lesions, wherein the heart valve is an aortic valve and extruding the anatomical surface model of the heart valve to a predetermined thickness comprises:

extruding an aortic root surface of the anatomical surface model of the heart valve to a standard thickness associated with the aortic root if the standard thickness associated with the aortic root is greater than or equal to a minimum thickness level associated with the 3D printer, extruding the aortic root surface of the anatomical surface model of the heart valve to the minimum thickness level associated with the 3D printer if the standard thickness associated with the aortic root is less than the minimum thickness level associated with the 3D printer, extruding aortic valve leaflet surfaces of the anatomical surface model of the heart valve to a standard thickness associated with the aortic valve leaflets if the standard thickness associated with the aortic valve leaflets is greater than or equal to the minimum thickness level associated with the 3D printer, and extruding the aortic valve leaflet surfaces of the anatomical surface model of the heart valve to the minimum thickness level associated with the 3D printer if the standard thickness associated with the aortic valve leaflets is less than the minimum thickness level associated with the 3D printer.

29. The non-transitory computer readable medium of claim 28, wherein controlling a 3D printer to create a 3D printed model of the heart valve and calcified lesions comprises:

controlling the 3D printer to create the 3D printed model of the heart valve and calcified lesions using a first material for heart valve tissue and a second material for the calcified lesions.

30. The non-transitory computer readable medium of claim 29, wherein the second material has a stiffness that is greater than the first material.

31. The non-transitory computer readable medium of claim 30, wherein the first material has a stiffness property equal to a standard value of a stiffness property of the heart valve tissue and the second material has a stiffness property equal to a standard value of a stiffness property of calcified lesions.

32. The non-transitory computer readable medium of claim 28, wherein estimating an anatomical surface model of a heart valve from medical image data of a patient comprises:

detecting a global location of a physiological model of the heart valve in the medical image data;

detecting anatomical landmarks of the heart valve in the medical image data based on the detected global location; and fitting a surface model of the heart valve to the medical image data based on the detected anatomical landmarks.

33. The non-transitory computer readable medium of claim 28, wherein segmenting calcified lesions within the heart valve in the medical image data comprises:

defining a heart valve region-of-interest in the medical image data based on the estimated anatomical surface model of the heart valve; and segmenting the calcified lesions within the heart valve region-of-interest in the medical image data.

34. The non-transitory computer readable medium of claim 33, wherein segmenting the calcified lesions within the heart valve region-of-interest in the medical image data comprises:

detecting voxels in the heart valve region-of-interest having intensity values greater than a calcium threshold.

35. The non-transitory computer readable medium of claim 34, wherein segmenting the calcified lesions within the heart valve region-of-interest in the medical image data further comprises:

determining the calcium threshold based on an intensity histogram in the heart valve region-of-interest of the medical image data.

36. The non-transitory computer readable medium of claim 28, wherein extruding the anatomical surface model of the heart valve to a predetermined thickness further comprises:

at each of a plurality of points on the anatomical surface model of the heart valve, extruding the anatomical surface model of the heart valve in a direction normal to the anatomical surface model of the heart valve.

37. The non-transitory computer readable medium of claim 28, wherein controlling a 3D printer to create a 3D printed model of the heart valve and calcified lesions comprises:

controlling the 3D printer to print a physical 3D model of the combined volumetric model of the heart valve and calcified lesions.

* * * * *